United States Patent
Kaneko

(10) Patent No.: US 10,347,372 B2
(45) Date of Patent: Jul. 9, 2019

(54) INFORMATION PROCESSING APPARATUS, INFORMATION PROCESSING METHOD, AND NON-TRANSITORY COMPUTER READABLE STORAGE MEDIUM

(71) Applicant: FUJI XEROX CO., LTD., Tokyo (JP)

(72) Inventor: Hiroyuki Kaneko, Kanagawa (JP)

(73) Assignee: FUJI XEROX CO., LTD., Tokyo (JP)

( * ) Notice: Subject to any disclaimer, the term of this patent is extended or adjusted under 35 U.S.C. 154(b) by 0 days.

(21) Appl. No.: 15/485,562

(22) Filed: Apr. 12, 2017

(65) Prior Publication Data

US 2018/0068073 A1 Mar. 8, 2018

(30) Foreign Application Priority Data

Sep. 2, 2016 (JP) .................................. 2016-171411

(51) Int. Cl.
*G06F 19/00* (2018.01)
*H04N 1/21* (2006.01)
*H04N 1/32* (2006.01)
*G16H 10/60* (2018.01)

(52) U.S. Cl.
CPC .......... *G16H 10/60* (2018.01); *G06F 19/321* (2013.01); *H04N 1/2179* (2013.01); *H04N 1/32128* (2013.01); *H04N 1/32272* (2013.01); *H04N 2201/0081* (2013.01); *H04N 2201/3226* (2013.01)

(58) Field of Classification Search
CPC combination set(s) only.
See application file for complete search history.

(56) References Cited

U.S. PATENT DOCUMENTS

| | | | |
|---|---|---|---|
| 2016/0216706 A1* | 7/2016 | Christensen | G05B 19/41865 |
| 2016/0239838 A1* | 8/2016 | Yang | G06Q 20/40 |
| 2016/0342439 A1* | 11/2016 | Woerndle | H04L 61/2596 |
| 2016/0344724 A1* | 11/2016 | Shoshan | H04L 63/0815 |
| 2017/0154075 A1* | 6/2017 | Anderson | G06F 17/30466 |
| 2017/0206322 A1* | 7/2017 | Kumar | G06F 19/322 |
| 2018/0076893 A1* | 3/2018 | Aoyama | H04B 10/116 |
| 2018/0096292 A1* | 4/2018 | DeBusk | G06Q 10/087 |

FOREIGN PATENT DOCUMENTS

| | | |
|---|---|---|
| JP | 2002-132563 A | 5/2002 |
| JP | 2014-139736 A | 7/2014 |

* cited by examiner

Primary Examiner — Helen Zong
(74) Attorney, Agent, or Firm — Oliff PLC

(57) ABSTRACT

An information processing apparatus includes an identifier generator, a reversible converter, and an assignment unit. The identifier generator generates first identifiers which are uniquely specified. The reversible converter reversibly converts the first identifiers to generate second identifiers. The assignment unit assigns the second identifiers to processes to be assigned with identifiers.

14 Claims, 4 Drawing Sheets

INFORMATION PROCESSING APPARATUS, INFORMATION PROCESSING METHOD, AND NON-TRANSITORY COMPUTER READABLE STORAGE MEDIUM

CROSS-REFERENCE TO RELATED APPLICATIONS

This application is based on and claims priority under 35 USC 119 from Japanese Patent Application No. 2016-171411 filed Sep. 2, 2016.

BACKGROUND

(i) Technical Field

The present invention relates to an information processing apparatus, an information processing method, and a non-transitory computer readable storage medium.

(ii) Related Art

An identifier may be assigned to an object to be assigned with an identifier, such as data.

SUMMARY

According to an aspect of the invention, an information processing apparatus includes an identifier generator, a reversible converter, and an assignment unit. The identifier generator generates first identifiers which are uniquely specified. The reversible converter reversibly converts the first identifiers to generate second identifiers. The assignment unit assigns the second identifiers to processes to be assigned with identifiers.

BRIEF DESCRIPTION OF THE DRAWINGS

Exemplary embodiments of the present invention will be described in detail based on the following figures, wherein.

DETAILED DESCRIPTION

Figure 1:
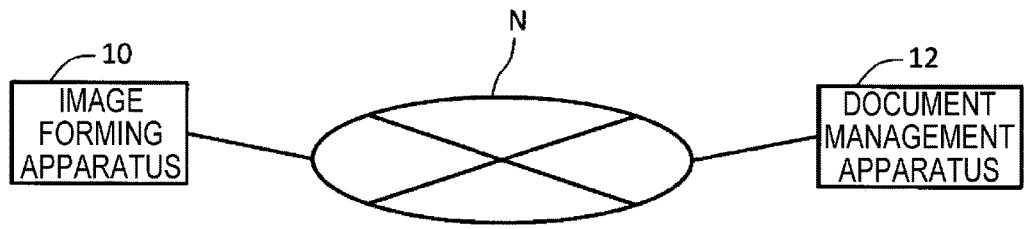
FIG. 1 is a block diagram illustrating a document management system according to an exemplary embodiment of the present invention.

As an information processing system according to an exemplary embodiment of the invention, a document management system will be described with reference to FIG. 1. FIG. 1 illustrates an example of the document management system according to the exemplary embodiment. The document management system includes an image forming apparatus 10 as an information processing apparatus and a document management apparatus 12. The image forming apparatus 10 and the document management apparatus 12 have, for example, a function of communicating with each other via a communication path N. In the example illustrated in FIG. 1, the document management system includes one image forming apparatus 10 and one document management apparatus 12. However, the document management system may include plural image forming apparatuses 10 and plural document management apparatuses 12. The document management system may well include other apparatuses.

The image forming apparatus 10 has a function of forming an image. The image forming apparatus 10 has at least one of, for example, a scanning function, a printing function, a copying function, and a facsimile function. Further, the image forming apparatus 10 has a function of transmitting/receiving data with other apparatuses. The image forming apparatus 10 has a wireless communication function such as the Wi-Fi® communication or a wired communication function, and has a function of transmitting/receiving data via a network such as the Internet or a local area network (LAN).

The document management apparatus 12 manages document data. The document data are, for example, text data including character strings, data including character strings and images, and image data. For example, document data generated by the scanning function of the image forming apparatus 10 is transmitted to the document management apparatus 12 and registered in the document management apparatus 12.

The communication path N is implemented by, for example, a network such as the Internet or the LAN.

In the document management system according to the exemplary embodiment, an identifier is generated for a process (transaction) performed between the image forming apparatus 10 and the document management apparatus 12, and the identifier is assigned to each process. For example, document data (e.g., document data generated by scanning a document) is generated by the image forming apparatus 10, and the document data is transmitted from the image forming apparatus 10 to the document management apparatus 12 to be registered (e.g., stored) in the document management apparatus 12. For example, a process of registering document data from the image forming apparatus 10 to the document management apparatus 12 or a process of acquiring document data by the image forming apparatus 10 (a process in which the image forming apparatus 10 acquires document data from the document management apparatus 12) corresponds to a process to be assigned with an identifier. An identifier is assigned to the registering process or the acquiring process.

The document management system according to the exemplary embodiment is, for example, a system for managing medical information, and the process to be assigned with an identifier is a process related to medical information. In this case, the image forming apparatus 10 is installed in a medical facility such as a hospital or a clinic. The process related to medical information is, for example, a process of registering medical information or a process of acquiring medical information. The medical information includes, for example, a document related to a medical care and information related to a patient. The document related to a medical care includes, for example, a patient referral document, a consent form, and a chart. The information related to a patient includes, for example, patient identification information for identifying a patient and basic patient information (e.g., name, gender, birth date, and address of a patient). The document management apparatus 12 manages document data related to a medical care, and furthermore, manages information related to a patient. For example, document data related to a medical care (e.g., document data generated by scanning a document related to a medical care)

is generated by the image forming apparatus 10, and the document data is transmitted from the image forming apparatus 10 to the document management apparatus 12 to be registered in the document management apparatus 12. For example, the process of registering or acquiring the document data corresponds to the process to be assigned with an identifier. In addition, the process in which the image forming apparatus 10 acquires information related to a patient from the document management apparatus 12 corresponds to the process to be assigned with an identifier. Other processes such as a process of registering information related to a patient in the document management apparatus 12 may correspond to the process to be assigned with an identifier.

The document management system according to the exemplary embodiment is applied to, for example, a healthcare community. For example, plural medical facilities are installed in a community to be managed by the document management system, and the image forming apparatus 10 is installed in each medical facility. In each medical facility, a patient ID which is used in the medical facility is issued as patient identification information for identifying a patient in the medical facility. Further, in the healthcare community, a community ID which is commonly used in a community to be managed by the document management system is issued as patient identification information for identifying a patient in the community. As described later, the document management apparatus 12 manages a patient ID used in each medical facility and a community ID commonly used in the community in association with each other. Hereinafter, descriptions will be made on the case where the document management system according to the exemplary embodiment is applied to the healthcare community.

Figure 2:
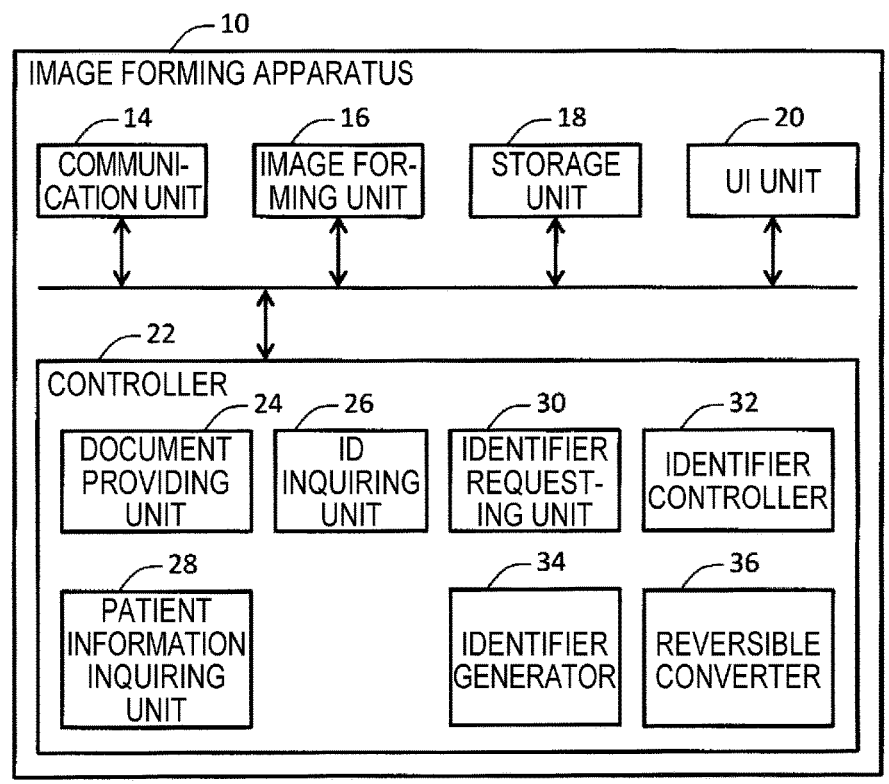
FIG. 2 is a block diagram illustrating an image forming apparatus according to the exemplary embodiment.

Hereinafter, the configuration of the image forming apparatus 10 will be described in detail with reference to FIG. 2. FIG. 2 illustrates the configuration of the image forming apparatus 10.

A communication unit 14 is a communication interface and has a function of transmitting data to other apparatuses and a function of receiving data from other apparatuses. The communication unit 14 has, for example, a wireless communication function such as the Wi-Fi communication or a wired communication function, and has a function of transmitting/receiving data via a network such as the Internet or the LAN.

An image forming unit 16 performs an image forming process. The image forming unit 16 performs at least one of, for example, a scanning function, a printing function, a copying function, and a facsimile function. When the scanning function is performed, a document is read, and document data (scanned data) is generated. When the printing function is performed, an image is printed on a recording medium such as paper. When the copying function is performed, a document is read and printed on a recording medium. When the facsimile function is performed, document data is transmitted or received by facsimile.

A storage unit 18 is a storage device such as a hard disk or a memory and stores performance instruction information (e.g., job information) indicating a performance instruction of the image forming process, document data to be printed, document data generated by scanning, various kinds of control data, various kinds of programs, various kinds of data and others. Of course, these information and data may be stored in separates storage devices or an identical storage device.

A UI unit 20 is a user interface unit and includes a display unit and an operation unit. The display unit is, for example, a display device such as a liquid crystal display. The operation unit is an input device such as a touch panel or a keyboard. Of course, the UI unit 20 may be a user interface (e.g., a display as a touch panel or a display for electronically displaying a keyboard or the like) having the functions of both the display unit and the operation unit.

A controller 22 has a function of controlling the operations of the respective units of the image forming apparatus 10. For example, the controller 22 causes the UI unit 20 to display various kinds of information. Further, the controller 22 includes a document providing unit 24, an ID inquiring unit 26, a patient information inquiring unit 28, an identifier requesting unit 30, an identifier controller 32, an identifier generator 34, and a reversible converter 36.

The document providing unit 24 has a function of providing document data to other apparatuses. For example, the image forming unit 16 generates document data by scanning a document, and the document providing unit 24 transmits the document data to the document management apparatus 12 via the communication path N. The document data is registered in the document management apparatus 12. As described above, the document to be scanned is a document related to a medical care (e.g., a patient referral document, a consent form, or a chart). The process of registering (providing) the document data by the document providing unit 24 corresponds to a process to be assigned with an identifier.

The ID inquiring unit 26 has a function of inquiring about a community ID corresponding to a patient ID from the document management apparatus 12 and acquiring the community ID from the document management apparatus 12, via the communication path N. The process of inquiring or acquiring the community ID by the ID inquiring unit 26 corresponds to a process to be assigned with an identifier.

The patient information inquiring unit 28 has a function of inquiring about basic patient information from the document management apparatus 12 and acquiring the basic patient information from the document management apparatus 12, via the communication path N. The basic patient information indicates, for example, the name, gender, birth date, and address of a patient. The process of inquiring or acquiring the basic patient information by the patient information inquiring unit 28 corresponds to a process to be assigned with an identifier.

The identifier requesting unit 30 has a function of requesting an identifier which is assigned to a process (transaction) to be assigned with an identifier, from the identifier controller 32. For example, when a process to be assigned with an identifier is performed between the image forming apparatus 10 and the document management apparatus 12, the identifier requesting unit 30 requests an identifier from the identifier controller 32. When document data is generated by scanning, the identifier requesting unit 30 may request an identifier to be assigned to the document data, from the identifier controller 32.

The identifier controller 32 has a function of instructing the identifier generator 34 and the reversible converter 36 to generate an identifier in response to the request from the identifier requesting unit 30.

The identifier generator 34 has a function of generating a first identifier which is a uniquely specified identifier. Here, the "uniquely specified identifier" is an identifier which does not require a confirmation of overlapping with identifiers issued in the past. The uniquely specified identifiers are, for example, consecutive numbers or date and time information having digits up to milliseconds. In the example described below, descriptions will be made on a case where "consecutive numbers" are used as uniquely specified identifiers. For example, the identifier generator 34 uses consecutive numbers as seeds (seed information) for the identifier generation and generates first identifiers each containing the corresponding consecutive number. The identifier generator 34 generates a first identifier for each of objects to be assigned with identifiers, according to the occurring order of the objects to be assigned with identifiers. For example, when a first identifier is generated in the order of 1, 2, 3, . . . , the digit "1" is used as a first identifier for a first occurring object to be assigned with an identifier, and the digit "2" is used as a first identifier for a second occurring object to be assigned with an identifier. The subsequent digits are used in the same manner as described above. For example, 64-bit consecutive numbers are used as seeds. The 64-bit consecutive numbers may express up to maximum of "18,446,744,073,709,551,616". Thus, even when communications (transactions) are conducted 10,000 times per second, and identifiers are assigned to the respective communications (respective transactions), the identifiers do not overlap with each other for 58 million years. As another example, date and time information having digits up to milliseconds may be used as a seed (seed information) for the identifier generation. In this case, when requests for identifiers are made at the same time, the identifier generator 34 performs an exclusive control not to generate identical time information. For example, when time in the millisecond unit from Jan. 1, 1970 is expressed in 64 bits, identifiers by maximum Aug. 17, 292278994 AC may be expressed.

The reversible converter 36 has a function of reversibly converting first identifiers (e.g., consecutive numbers or date and time information) which are uniquely specified, so as to generate second identifiers. Since the reversible conversion may return the converted information back to the original information, the second identifiers generated by the reversible conversion have a one-to-one relationship with the original consecutive numbers (the first identifiers). As a result, the uniqueness of an identifier is maintained, and the confirmation of overlapping with already issued identifiers is unnecessary. For example, an encryption algorithm is used as an algorithm for the reversible conversion. As the encryption algorithm, for example, a common key cryptosystem such as "Blowfish" is used. Of course, another encryption algorithm may be used. When a first identifier is encrypted with "Blowfish", 64-bit binary data is generated. Thus, even when a first identifier is encrypted consecutively with, for example, 1, 2, 3, . . . , binary data generated by the encryption becomes irregular, like random numbers. In general, an identifier is expressed by a character string. Thus, when the binary data generated by the encryption is encoded with "Base32", the identifier is expressed as "bb4lrs4v32cye===". In the identifier, "===" is a padding necessary for decoding. Since the decoding is not performed, when "===" is deleted, and the character string from which "===" has been deleted is used as an identifier, the identifier is expressed by 13 alphanumeric characters. The encoding and the deletion of the padding "===" are performed by the reversible converter 36.

When the second identifier is generated as described above, the identifier requesting unit 30 functions as an assigning unit, and assigns the second identifier generated by the reversible converter 36 to a process to be assigned with an identifier.

Figure 3:
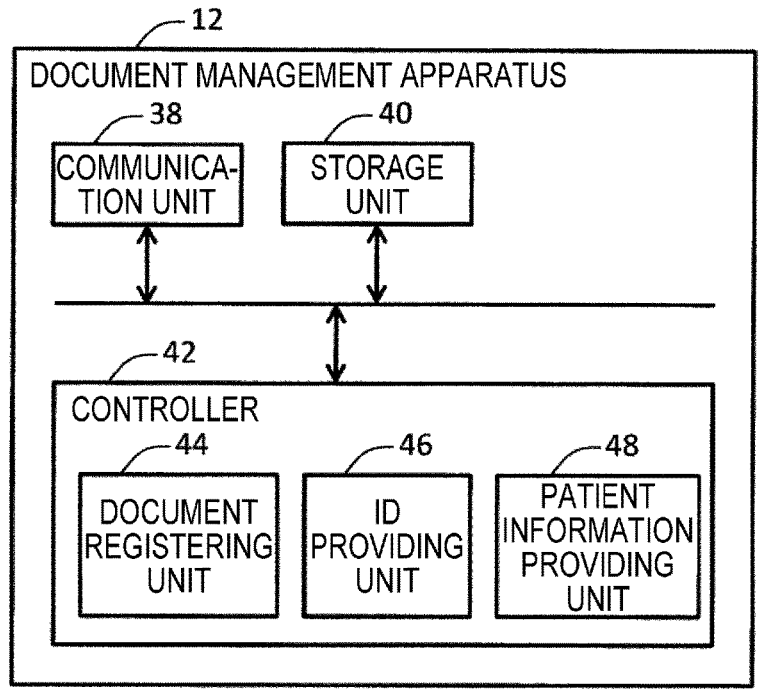
FIG. 3 is a block diagram illustrating a document management apparatus according to the exemplary embodiment.

Hereinafter, the configuration of the document management apparatus 12 will be described in detail with reference to FIG. 3. FIG. 3 illustrates the configuration of the document management apparatus 12.

A communication unit 38 is a communication interface and has a function of transmitting data to other apparatuses and a function of receiving data from other apparatuses. The communication unit 38 has, for example, a wireless communication function such as the Wi-Fi communication or a wired communication function, and has a function of transmitting/receiving data via a network such as the Internet or the LAN.

A storage unit 40 is a storage device such as a hard disk or a memory and stores, for example, document data, patient identification information, and basic patient information. The document data is data that is generated by the image forming apparatus 10 installed in each medical facility and transmitted to the document management apparatus 12. The document data is associated with, for example, a community ID. Associating the document data and a community ID with each other is performed by, for example, the image forming apparatus 10. For example, when document data generated by the image forming apparatus 10 is registered in the document management apparatus 12, the image forming apparatus 10 associates the document data with a community ID. Of course, the associating may be performed by the document management apparatus 12. In addition, the storage unit 40 stores, as the patient identification information, medical facility identification information (e.g., a medical facility ID) for identifying a medical facility, a patient ID used in the medical facility, and a community ID in association with each other. The associating is performed, for example, in advance. For example, when a patient in a certain medical facility is registered in the document management system, a patient ID of the patient which is used in the medical facility is input to the document management apparatus 12. A controller 42 of the document management apparatus 12 issues a community ID for commonly identifying the patient in the community, and the patient ID and the community ID are stored in association with each other as patient identification information in the storage unit 40. The basic patient information (e.g., information indicating name, gender, birth date, and address of a patient) is associated with a community ID. The associating is performed, for example, in advance. For example, when a patient is registered in the document management system, basic patient information is input to the document management apparatus 12, and the controller 42 of the document management apparatus 12 stores the basic patient information and a community ID of the patient in association with each other in the storage unit 40. The document data, the patient identification information, the basic patient information and others may be stored in separate storage devices or in an identical storage device.

The controller 42 has a function of controlling the operations of the respective units of the document management apparatus 12. Further, the controller 42 includes a document registering unit 44, an ID providing unit 46, and a patient information providing unit 48.

The document registering unit 44 has a function of registering document data in the storage unit 40. For example, the document registering unit 44 stores document data transmitted from the image forming apparatus 10 in the storage unit 40.

The ID providing unit 46 has a function of providing a community ID to the image forming apparatus 10 in response to an inquiry about a community ID from the image forming apparatus 10.

The patient information providing unit 48 has a function of providing basic patient information to the image forming apparatus 10 in response to an inquiry about basic patient information from the image forming apparatus 10.

For example, each of the process between the document providing unit 24 of the image forming apparatus 10 and the document registering unit 44 of the document management apparatus 12 (e.g., the process of registering (providing) document data), the process between the ID inquiring unit 26 of the image forming apparatus 10 and the ID providing unit 46 of the document management apparatus 12 (e.g., the inquiring processor the acquiring process), and the process between the patient information inquiring unit 28 of the image forming apparatus 10 and the patient information providing unit 48 of the document management apparatus 12 (e.g., the inquiring process or the acquiring process) corresponds to a process (transaction) to be assigned with an identifier. An identifier (a second identifier) is assigned to a performed process every time a process to be assigned with an identifier is performed. For example, the controller 42 of the document management apparatus 12 manages a performance history of each process to which an identifier (a second identifier) has been assigned (history information indicating a performance history).

Figure 5:
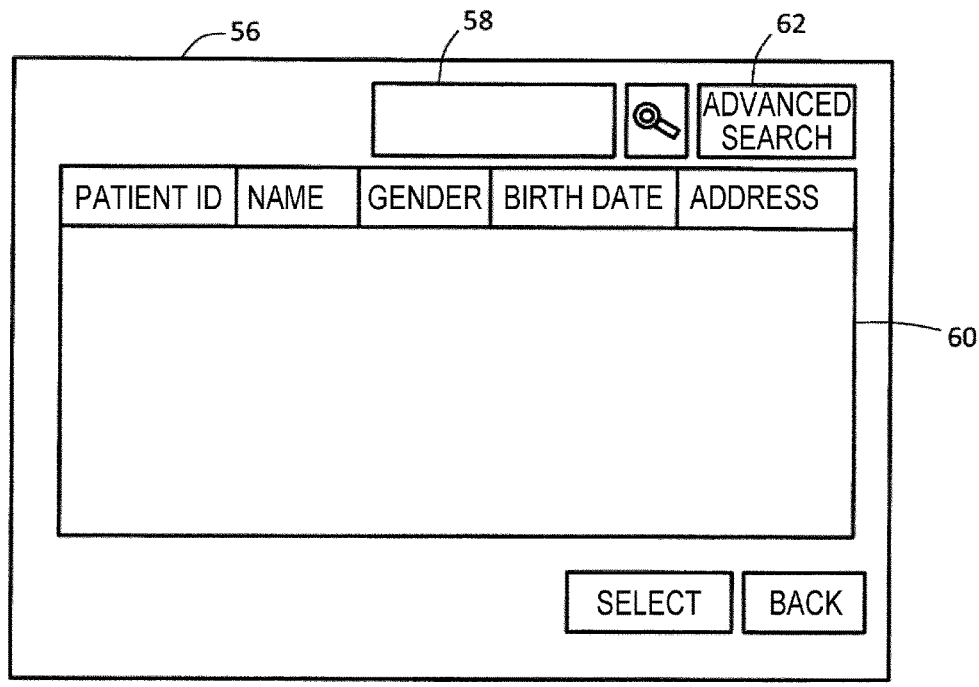
FIG. 5 is a view illustrating an exemplary patient list screen.
Figure 6:
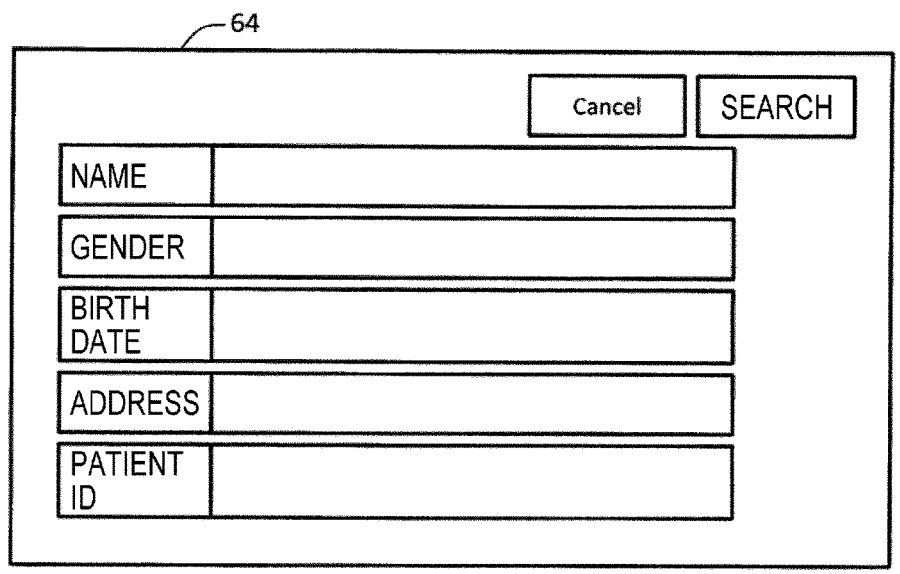
FIG. 6 is a view illustrating an exemplary patient advanced search screen.

Hereinafter, the process of registering document data will be described in detail with reference to FIGS. 4 to 6.

First, in the image forming apparatus 10, the controller 22 causes the UI unit 20 to display a menu screen. The menu screen displays a button image for instructing, for example, the process of registering document data (e.g., a document registration icon). When a user instructs the process of registering document data by using the UI unit 20 (e.g., when a user presses the icon), the controller 22 causes the UI unit 20 to display a scan setting screen. On the scan setting screen, a scanning condition such as a resolution may be set by the user. When the scanning condition is set, and the user makes an instruction to start the scanning, the image forming unit 16 generates document data by scanning a document to be registered (e.g., a patient referral document, a consent form, or a chart).

When document data is generated by the scanning, the controller 22 causes the UI unit 20 to display a preview screen. FIG. 4 illustrates a preview screen 50. The preview screen 50 displays, for example, a preview image 52 of the scanned document and an input field 54 for inputting information to be associated with the document data. In the input field 54, the user may input, for example, a name of the medical facility, a name of a department, a generation (creation) date of document data, a document type, and patient identification information (e.g., a patient ID used in the medical facility or a name of a patient). The input information is associated with the document data.

In addition, there is a case where coded information such as a two-dimensional barcode has been printed on the document to be scanned. The coded information may include, for example, a patient ID used in the medical facility. In this case, when the coded information is read by scanning, the controller 22 acquires the patient ID from the coded information and causes the patient ID to be displayed in the input field 54. When the patient ID is not acquired by the scanning of the document, a portion of the input field 54 in which the patient identification information is to be input is left blank.

When the user designates the portion of the input field 54 in which the patient identification information is to be input, the controller 22 causes the UI unit 20 to display a patient list screen. FIG. 5 illustrates a patient list screen 56. The patient list screen 56 displays a patient ID input field 58, a patient display field 60, and an advanced search button image 62 (e.g., an advanced search icon).

When the user inputs a patient ID used in the medical facility to the patient ID input field 58 and makes a search instruction, the ID inquiring unit 26 inquires a community ID corresponding to the input patient ID from the document management apparatus 12 and acquires the community ID from the document management apparatus 12. The acquired community ID is associated with the document data as described later. Each of the processes of inquiring and acquiring the community ID corresponds to a process to be assigned with an identifier. Every time the processes of inquiring and acquiring a community ID are performed, a first identifier is generated by the identifier generator 34, and a second identifier is generated by the reversible converter 36 and assigned to each of the processes. The second identifier is assigned to the process of inquiring or acquiring a community ID by the image forming apparatus 10, and the history information indicating a performance history of the process of inquiring or acquiring a community ID is managed by, for example, the document management apparatus 12.

The controller 22 causes the list of the patient ID to be displayed in the patient display field 60. For example, the controller 22 acquires a patient ID of a patient in the medical facility and displays the patient ID in the patient display field 60. When a specific patient is selected by the user from the information displayed in the patient display field 60 (e.g., when a specific patient is designated by the user and a select button image is pressed), the controller 22 causes the UI unit 20 to display the preview screen 50 illustrated in FIG. 4 and causes information related to the patient selected by the user (e.g., a patient ID) to be displayed in the portion of the input field 54 in which the patient identification information is to be input. In addition, in a case where the community ID has not been acquired, when a specific patient is selected by the user, the ID inquiring unit 26 acquires the community ID associated with the patient ID of the specific patient from the document management apparatus 12.

In addition, when the user presses the advanced search button image 62 on the patient list screen 56, the controller 22 causes the UI unit 20 to display a patient advanced search screen. FIG. 6 illustrates a patient advanced search screen 64. The patient advanced search screen 64 displays fields for inputting, for example, a name, a gender, a birth date, an address, and a patient ID, as fields for inputting the information related to the patient. When the user inputs the information related to the patient and instructs a search (e.g., when the user presses a search button image), the patient information inquiring unit 28 inquires basic patient information corresponding to the input information from the document management apparatus 12 and acquires the basic patient information from the document management apparatus 12. When the basic patient information is acquired, the controller 22 causes the UI unit 20 to display the patient list screen 56 illustrated in FIG. 5 and causes the search result (the acquired basic patient information) to be displayed in the patient display field 60. When a specific patient is selected by the user from the information displayed in the patient display field 60, the controller 22 causes the UI unit 20 to display the preview screen 50 illustrated in FIG. 4 and causes the information related to the patient selected by the user (e.g., the patient ID) to be displayed in the portion of the input field 54 in which the patient identification information is to be input. In addition, in a case where the community ID has not been acquired, when a specific patient is selected by the user, the ID inquiring unit 26 acquires the community ID associated with the patient ID of the specific patient from the document management apparatus 12.

Each of the processes of inquiring and acquiring the basic patient information corresponds to a process to be assigned with an identifier. Every time the processes of inquiring and acquiring the basic patient information are performed, a first identifier is generated by the identifier generator 34, and a second identifier is generated by the reversible converter 36 and assigned to each of the processes. The second identifier is assigned to the process of inquiring or acquiring the basic patient information by the image forming apparatus 10, and the history information indicating a performance history of the process of inquiring or acquiring the basic patient information is managed by, for example, the document management apparatus 12.

Figure 4:
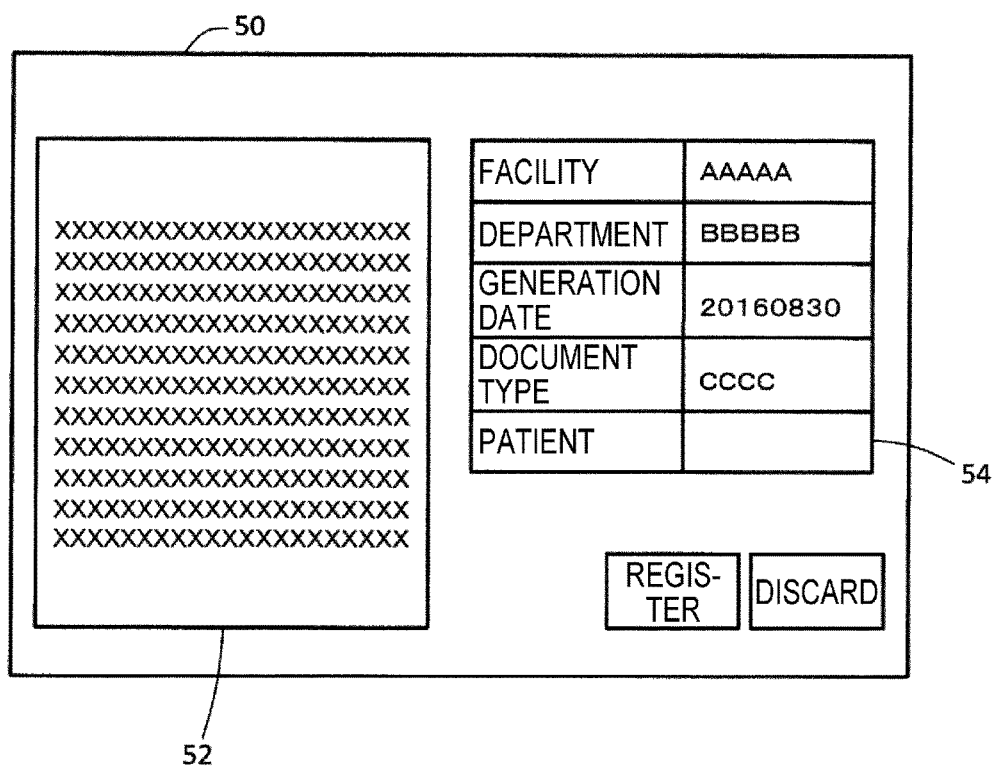
FIG. 4 is a view illustrating an exemplary preview screen.

When the user instructs registration on the preview screen 50 illustrated in FIG. 4 (e.g., when the user presses a registration button image), the document providing unit 24 transmits the document data to be registered to the document management apparatus 12. The document data is registered in the document management apparatus 12. Since the community ID has been acquired as described above, the document providing unit 24 associates the document data to be registered with the community ID and transmits the document data to the document management apparatus 12. The process of registering (providing) the document data corresponds to a process to be assigned with an identifier. Every time the process of registering the document data is performed, a first identifier is generated by the identifier generator 34, and a second identifier is generated by the reversible converter 36 and assigned to the process of registering the document data. The second identifier is assigned to the process of registering the document data by the image forming apparatus 10, and the history information indicating a performance history of the process of registering the document data is registered in, for example, the document management apparatus 12. Since the document data has been associated with the community ID, the document data is searched by designating the community ID. In addition, since the medical facility ID and the patient ID have been associated with the community ID, the document data is searched by designating the medical facility ID and the patient ID.

In addition, when the document data is generated by scanning, a first identifier may be generated by the identifier generator 34, and a second identifier may be generated by the reversible converter 36 and assigned to the document data. In this case, the document data to which the second identifier has been assigned is registered in the document management apparatus 12.

Figure 7:
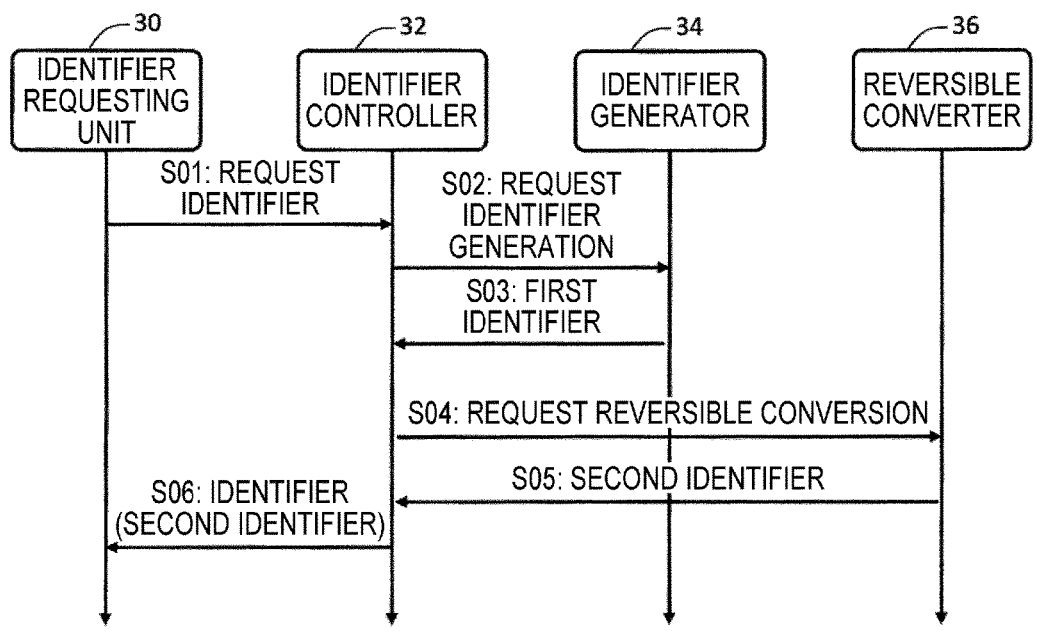
FIG. 7 is a sequence view illustrating an identifier generating process according to the exemplary embodiment.

Hereinafter, the identifier generating process by the image forming apparatus 10 will be described in detail with reference to FIG. 7. FIG. 7 is a sequence view illustrating the process.

First, when an event requiring the generation of an identifier occurs, the identifier requesting unit 30 requests an identifier to be assigned to an object to be assigned with an identifier, from the controller 32 (S01). The event requiring the generation of an identifier is, for example, the process of registering document data, the process of inquiring or acquiring a community ID, or the process of inquiring or acquiring basic patient information as described above.

The identifier controller 32 requests the generation of an identifier from the identifier generator 34 in response to the request from the identifier requesting unit 30 (S02).

In response to the request from the identifier controller 32, the identifier generator 34 generates a first identifier which is uniquely specified and outputs the first identifier to the identifier controller 32 (S03). The identifier generator 34 performs an exclusive control for the identifier in order not to generate plural first identifiers having the same value. Accordingly, a first identifier having a different value from other first identifiers is generated. For first identifiers, different values such as consecutive numbers 1, 2, 3, . . . or time information (e.g., information indicating year, month, day, and time (hour, minute, and second)) are used. The time information may be, for example, information having the unit of milliseconds. Here, as an example, it is assumed that the value "1" of the consecutive numbers is used as the first identifier. Of course, date and time information may be used as the first identifier.

When receiving the first identifier from the identifier generator 34, the identifier controller 32 requests a reversible conversion from the reversible converter 36 (S04). At this time, the first identifier is output from the identifier controller 32 to the reversible converter 36.

In response to the request from the identifier controller 32, the reversible converter 36 reversibly converts the first identifier so as to generate a second identifier, and outputs the second identifier to the identifier controller 32 (S05). By performing the reversible conversion, the first identifier and the second identifier have a one-to-one relationship with each other. Here, as an example, when Blowfish is used as the reversible conversion algorithm, and an encryption key is {0x0, 0x1, 0x2, 0x3, 0x4, 0x5, 0x6, 0x7}, the second identifier becomes {0x42, 0x0e, 0x6f, 0x98, 0x94, 0xd0, 0x44, 0x15}. When a hexadecimal character string is used as the second identifier, a second identifier having 16 characters is generated, and the identifier generating process is ended. The reversible converter 36 may generate a second identifier having 13 characters by encoding the binary data generated by the encryption with "Base32" and deleting the padding "===".

When receiving the second identifier from the reversible converter 36, the identifier controller 32 outputs the second identifier to the identifier requesting unit 30 (S06). The identifier requesting unit 30 assigns the second identifier to a process to be assigned with an identifier (e.g., a performed process). For example, when the process of registering (providing) document data is performed by the document providing unit 24, the second identifier is assigned to the registering process, and the history information indicating a performance history of the registering process is managed by, for example, the document management apparatus 12.

As described above, according to the exemplary embodiment, the first identifiers (e.g., the consecutive numbers or the date and time information) which are uniquely specified are used as the seeds for the identifier generation so that identifiers having a sequential relationship among the identifiers are generated. Further, by reversibly converting the first identifier, a second identifier having a one-to-one relationship with the original first identifier is generated. Therefore, the uniqueness of an identifier is maintained, and the confirmation of overlapping with already issued identifiers is unnecessary. Further, since the second identifier is randomized by the reversible conversion (e.g., the encryption algorithm), even when the second identifier is assigned to a process (transaction) or document data, it is difficult to conceive an existence of other processes or document data from the second identifier. Hence, the security of information related to other processes or other document data is improved, as compared to a case where identifiers simply containing consecutive numbers are assigned to processes or document data. For example, when a second identifier is assigned to the process of registering document data, it is difficult to conceive an existence of other processes of registering document data, i.e., an existence of other document data, from the second identifier. Therefore, the security of other document data is improved.

Consecutive numbers in different value ranges may be assigned in advance to respective medical facilities to be managed by the document management system according to the exemplary embodiment. That is, consecutive numbers in different value ranges are assigned to respective image forming apparatuses 10 installed in medical facilities. For example, consecutive numbers "1 to 10000" are assigned to a medical facility A, and consecutive numbers "10001 to 20000" are assigned to a medical facility B. The storage unit 18 of each image forming apparatus 10 stores information indicating consecutive numbers assigned to a medical facility where the own apparatus is installed. For example, the storage unit 18 of the image forming apparatus 10 installed in the medical facility A stores information indicating the consecutive numbers "1 to 10000", and the storage unit 18 of the image forming apparatus 10 installed in the medical facility B stores information indicating the consecutive numbers "10001 to 20000".

The identifier generator 34 of the image forming apparatus 10 generates a first identifier by using the number assigned to the medical facility where the own apparatus is installed, and the reversible converter 36 generates a second identifier by reversibly converting the first identifier. For example, the identifier generator 34 of the image forming apparatus 10 installed in the medical facility A generates a first identifier by using a number from the consecutive numbers "1 to 10000", and the reversible converter 36 generates a second identifier by reversibly converting the first identifier. The identifier generator 34 of the image forming apparatus 10 installed in the medical facility B generates a first identifier by using a number from the consecutive numbers "10001 to 20000", and the reversible converter 36 generates a second identifier by reversibly converting the first identifier.

As described above, since consecutive numbers in different value ranges are assigned to respective medical facilities, even when second identifiers are generated for the respective medical facilities, plural identical second identifiers are not generated for the plural medical facilities. That is, overlapping second identifiers are not generated. Therefore, the uniqueness of an identifier is maintained in the healthcare community implemented by plural medical facilities. In the above-described example, since the consecutive numbers "1 to 10000" are assigned to the medical facility A, and the consecutive numbers "10001 to 20000" are assigned to the medical facility B, second identifiers having different values are generated for the medical facilities A and B. Therefore, overlapping second identifiers are not generated between the medical facilities A and B, and the uniqueness of each identifier is maintained.

In the above-described example, the document management system according to the exemplary embodiment is applied to the healthcare community. However, the document management system according to the exemplary embodiment may be applied to a system other than the healthcare community, and a second identifier may be assigned to an object to be assigned with an identifier, such as each process or data.

Each of the image forming apparatus 10 and the document management apparatus 12 is implemented by, for example, the cooperation of hardware and software. Specifically, each of the image forming apparatus 10 and the document management apparatus 12 includes one or plural processors such as a CPU (not illustrated). When one or plural processors read and execute a program stored in a storage device (not illustrated), the functions of the respective units of the image forming apparatus 10 and the document management apparatus 12 are implemented. The program is stored in the storage device via a recording medium such as a CD or a DVD, or via a communication path such as a network. As another example, each of the units of the image forming apparatus 10 and the document management apparatus 12 may be implemented by a hardware resource such as a processor or an electronic circuit. For the implementation, a device such as a memory may be used. As another example, each of the units of the image forming apparatus 10 and the document management apparatus 12 may be implemented by, for example, a digital signal processor (DSP) or a field programmable gate array (FPGA).

The foregoing description of the exemplary embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. An information processing apparatus comprising:
a processor programmed to:
  generate first identifiers which are uniquely specified;
  reversibly convert the first identifiers to generate second identifiers, the first identifiers and the second identifiers being both unique, and a respective one of the second identifiers having a one-to-one relationship with a corresponding one of the first identifiers such that a confirmation of overlapping with an already issued identifier is unnecessary; and
  assign the second identifiers to processes to be assigned with identifiers, the processes to be assigned with identifiers including an exchange of data between the information processing apparatus and a different device, such that two different instances of data exchange between the information processing apparatus and the different device are assigned with two distinct pairs of the first and second identifiers.

2. The information processing apparatus according to claim 1, wherein the first identifiers are consecutive numbers.

3. The information processing apparatus according to claim 1, wherein the first identifiers are data and time information.

4. The information processing apparatus according to claim 1, wherein the processor is programmed to:
every time one of the processes to be assigned with identifiers is performed:
  generate a new first identifier for each performed process;
  generate a new second identifier for each performed process by reversibly converting the new first identifier; and
  assign the new second identifier to each performed process.

5. The information processing apparatus according to claim 1, wherein the processes to be assigned with identifiers are processes related to medical information.

6. The information processing apparatus according to claim 5, wherein the processes related to the medical information are processes of registering the medical information.

7. The information processing apparatus according to claim 6, wherein the processor is programmed to:
read documents related to a medical care to generate document data as the medical information the registering processes being processes of registering the generated document data in the different device that is external to the information processing apparatus; and
assign the second identifiers to the processes of registering the generated document data in the different device.

8. The information processing apparatus according to claim 5, wherein
consecutive numbers in different value ranges are assigned to respective medical facilities in advance; and
the processor is programmed to generate the first identifiers by using the consecutive numbers assigned to a medical facility where the information processing apparatus is installed.

9. The information processing apparatus according to claim 1, wherein the processor is programmed to reversibly convert the first identifiers by using an encryption algorithm to generate the second identifiers.

10. The information processing apparatus according to claim 9, wherein the encryption algorithm is a common key cryptosystem.

11. An information processing method comprising:
generating first identifiers which are uniquely specified;
reversibly converting the first identifiers to generate second identifiers, the first identifiers and the second identifiers being both unique, and a respective one of the second identifiers having a one-to-one relationship with a corresponding one of the first identifiers such that a confirmation of overlapping with an already issued identifier is unnecessary; and
assigning the second identifiers to processes to be assigned with identifiers, the processes to be assigned with identifiers including an exchange of data between an information processing apparatus and a different device, such that two different instances of data exchange between the information processing apparatus and the different device are assigned with two distinct pairs of the first and second identifiers.

12. A non-transitory computer readable storage medium storing a program causing a computer to execute information processing comprising:
generating first identifiers which are uniquely specified;
reversibly converting the first identifiers to generate second identifiers, the first identifiers and the second identifiers being both unique, and a respective one of the second identifiers having a one-to-one relationship with a corresponding one of the first identifiers such that a confirmation of overlapping with an already issued identifier is unnecessary; and
assigning the second identifiers to processes to be assigned with identifiers, the processes to be assigned with identifiers including an exchange of data between an information processing apparatus and a different device, such that two different instances of data exchange between the information processing apparatus and the different device are assigned with two distinct pairs of the first and second identifiers.

13. The information processing apparatus according to claim 1, wherein the processes to be assigned with identifiers are transactions between the information processing apparatus and the different device connected to the information processing apparatus via a network.

14. The information processing apparatus according to claim 13, wherein:
the transactions include at least one of (i) transmission of data by the information processing apparatus to the different device for registration and (ii) acquisition of the data by the information processing apparatus from the different device; and
transactions (i) and (ii) are each assigned with a distinct second identifier.

* * * * *